United States Patent

Schöning et al.

[11] Patent Number: 6,024,924
[45] Date of Patent: Feb. 15, 2000

[54] BIOSENSOR SYSTEM FOR DETECTING ORGANIC TRACE COMPOUNDS PRODUCED BY SMOLDERING FIRES

[75] Inventors: Michael Schöning, Jülich; Stefan Schütz, Giessen; Armin Riemer, Grevenbroich; Bernhard Weissbecker, Gründau; Axel Schwarz, Giessen; Marion Thust, Köln; Claus-Dieter Kohl; Hans Hummel, both of Giessen; Peter Kordos, Jülich; Hans Lüth, Aachen, all of Germany

[73] Assignee: Forschungzentrum Jülich GmbH, Jülich, Germany

[21] Appl. No.: 09/049,434

[22] Filed: Mar. 27, 1998

Related U.S. Application Data

[63] Continuation-in-part of application No. PCT/DE96/01799, Sep. 18, 1996, and a continuation-in-part of application No. PCT/DE96/01800, Sep. 18, 1996.

[30] Foreign Application Priority Data

Sep. 29, 1995 [DE] Germany ............... 195 36 384
Sep. 29, 1995 [DE] Germany ............... 195 36 389

[51] Int. Cl.⁷ .................................. G01N 27/00
[52] U.S. Cl. .................. 422/90; 340/634; 435/7.21
[58] Field of Search .................. 422/90, 98, 88; 340/634; 435/7.21

[56] References Cited

U.S. PATENT DOCUMENTS

| | | | |
|---|---|---|---|
| 4,877,582 | 10/1989 | Oda et al. | 422/68 |
| 4,882,292 | 11/1989 | Sudholter et al. | 437/42 |
| 5,140,393 | 8/1992 | Hijikihigawa et al. | 357/25 |
| 5,331,310 | 7/1994 | Stetter et al. | 340/632 |

OTHER PUBLICATIONS

Buch, R.M. "Neuronal Biosensors" Analytical Chemistry, vol. 61, No. 8, pp. 553A–542A (Apr. 1989).

*Primary Examiner*—Jeffrey Snay
*Attorney, Agent, or Firm*—Klaus J. Bach

[57] ABSTRACT

In a biosensor system for detecting trace compounds resulting from a fire or from plants damaged by destructive insects, a live chemoreceptor is provided for sensing the trace compounds, and a semiconductor component is connected to the chemoreceptor for providing sensor signals when the chemoreceptor senses the presence of trace compounds.

10 Claims, 1 Drawing Sheet

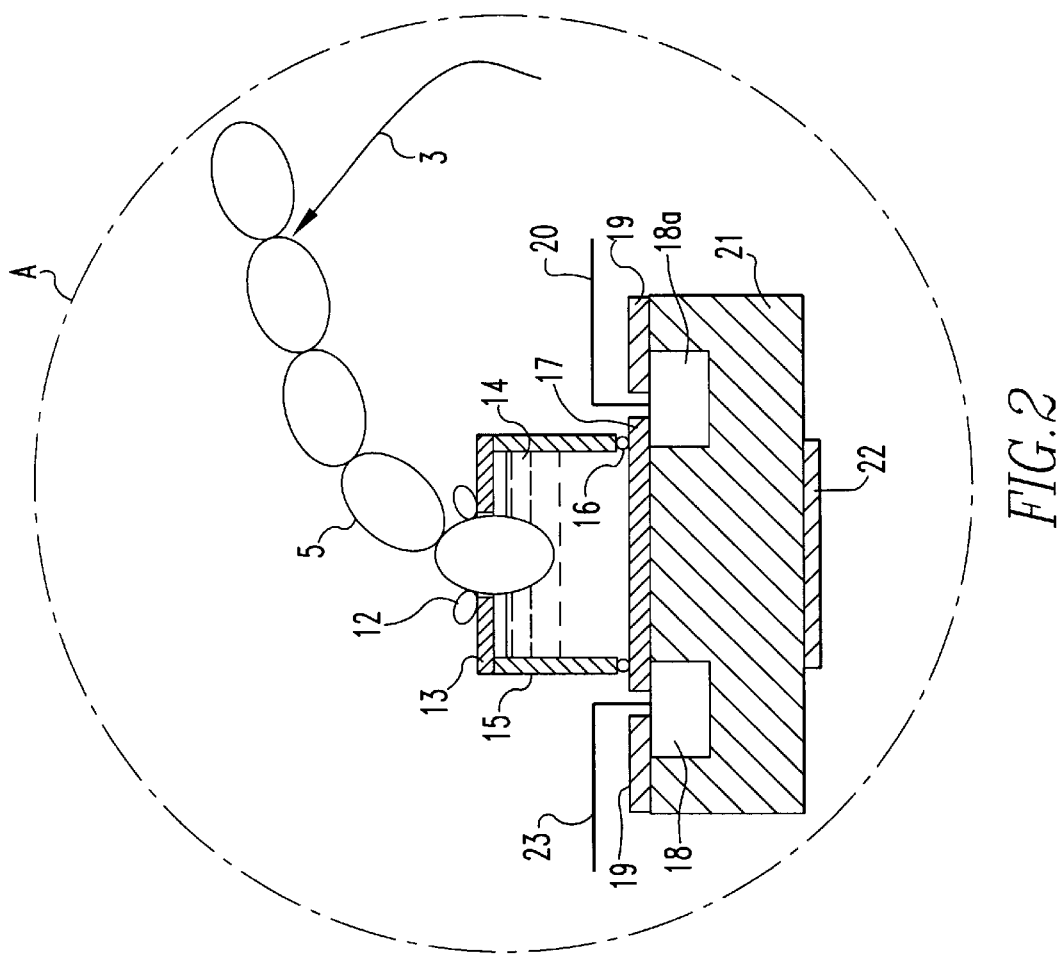
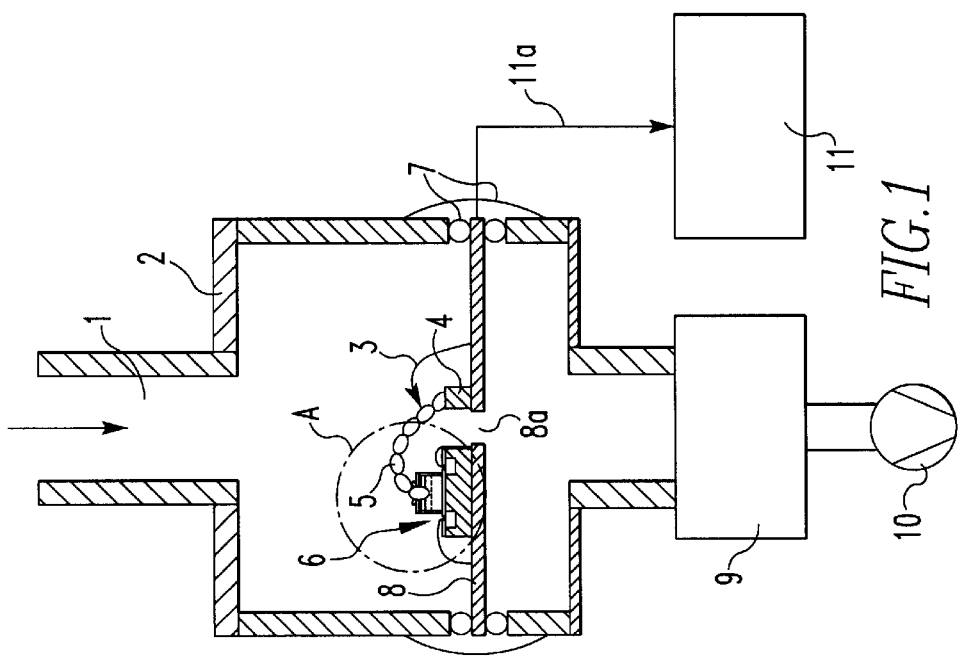

BIOSENSOR SYSTEM FOR DETECTING ORGANIC TRACE COMPOUNDS PRODUCED BY SMOLDERING FIRES

This is a Continuation-in-Part application of international applications PCT/DE96/01799 and PCT/DE96/01800 both filed Sep. 18, 1996 and claiming the priority of German applications 195 36 384.1 and 195 36 389.2 both filed Sep. 29, 1995.

BACKGROUND OF THE INVENTION

The invention relates to a biosensor system for detecting organic trace compounds particularly organic components in air resulting from smoldering fires or from plant damage utilizing a chemoreceptor.

Methods for the early detection of fires generally utilize optical sensors which measure the light scattering of aerosols. However, these methods have only limited reliability. Ionization detectors to measure the ionization current of ionized aerosols, which employ a radioactive preparation, are used less and less now.

The main reason herefor is the costly handling of the radioactive preparations. Thermocameras with which a temperature rise of 0.1° C. can be detected over a large area, are also used for example for the surveillance of stored waste materials in waste combustion plants. However, such camera systems are expensive while their reliability is questionable. Recently, gas sensors on the basis of semi-conductors or electrochemical cells are increasingly used. They are used to measure the concentration of CO, of $H_2$ with catalytically active surfaces, or of hydrocarbons. The detection sensitivity is about 1 ppm, the sensing reliability however may be detrimentally affected to various degrees by background gases such as motor vehicle exhaust gases (D. Kohl et al.: Gassorentechnik zur Erkenning von Schwelbraänden (gas sensor technique for the detection of smoldering fires) in "Brandmeldeanlagen", Vol 5 convention 1993).

It is a disadvantage of the known detection methods particular in the field of early fire detection that there is an insufficient selectivity and sensitivity for the substances which are sensed to provide adequate warming. In order to increase the detection reliability sensors are needed which permit the fire-specific detection of trace compounds with increased sensitivity.

It is furthermore problematic in integrated plant protection systems to determine the optimal point in time when to apply insecticides such that the least possible amount of insecticides is required and the chances for the destructive insects to become resistant to the insecticide are reduced.

Because of the great economical and ecological importance of this problem for the production of plants, various methods have been developed which are designed to determine the best point in time for treatment (R. L. Metcalf et al., Introduction of insect pest management, John Worley, & Sons, New York 1975).

These methods require either to walk the fields regularly and determine the population density by counting out the insects, or they utilize complicated computer simulation models of the insect population development which, however, can be utilized only locally and only in connection with particular types. A more universal method for determining the most suitable point in time for the application of insecticides resides in measuring the extent of the scent emissions generated by the plants as a result of their injuries. These emissions can be measured by conventional trace analysis methods such as gas chromatography in combination with mass spectroscopy (GC-MS) as well as by electroantennograms (EAG).

With the GC-MS method frequently used for trace analysis (J. Arey et al., Terpenes emitted from agricultural species found in California's Central Valley, J. Geoph. Res. 96 (1991) 9239-36), a high reliability and sensitivity is achieved on one hand, but on the other hand, the personnel and equipment costs as well as the time and space requirements are high as the equipment is voluminous and heavy. In contrast, the EAG method provides for a fast and highly sensitive detection of emissions in the range below 1 ppm as reported already by S. Schtitz et al. in Biosenser for plant damage by insects, Med. Fa. Lanbouww. University Gent, Belgium, 59/25(1994).

In this method, an insect is firmly held in place and the voltage drop at the insect antenna is measured by attaching a microelectrode to the free end of the insect antenna and another microelectrode to the end of the antenna adjacent the insect head. The electrodes are connected, by connecting wires, to a special signal processing unit which measures the depolarization voltage of the insect antenna in a time dependent manner while air containing trace components flows past the antenna.

This arrangement however, is electrically and mechanically unreliable and the life of the biosensitive component is only relatively short because of inappropriate adaptation of the insect antenna to the signal sensing electrodes. As a result, the arrangement has little flexibility in its operation and handling. In addition, the arrangement requires the use of micromanipulators for the stable coupling of the electrodes to the antenna. Also, the microelectrodes are very sensitive as they consist for example of glass and have a diameter of only, for example, 1 $\mu$m.

It is the object of the present invention to provide a biosensor and a suitable method of making a biosensor which has a high sensitivity and selectivity and which is highly reliable and which is furthermore portable for use in the field as a detector for example for plant emissions and for fire-specific emissions such as multi-functional phenols alkenes or terpenes.

SUMMARY OF THE INVENTION

In a biosensor system for detecting trace compounds a live chemoreceptor is provided for sensing the trace compounds and a semiconductor component is connected to the chemoreceptor for providing sensor signals when the chemoreceptor senses the presence of trace compounds.

The biosensor system is suitable for example the early detection of fires. It is based on the detection of organic compounds which are released in the early phase of a fire (detection of fire smell).

It is also suitable for measuring the emissions of plants caused by injuries, for example by destructive insects. These emissions include for example terpenes and leaf alcohols. It permits a determination of the type and extent of plant injuries and permits therefore the selection of the optimal point in time for the application of insecticides.

The biosensor system includes means for the admission of air, a biocomponent, a semiconductor component, a sampling cell arrangement and a signal and measurement value processor. The air sample admission means facilitates taking a well defined sample for measurement by the biocomponent. The biocomponent consists of an operative (live) chemoreceptor such as the antenna of a bark or a potato beetle. The chemoreceptor may be connected to the semiconductor component in a DC circuit or in an AC circuit (for example, in a capacitive or an inductive manner).

The recognition mechanism is activated after passage of a compound through the pores of the protective Chitin-Cuticula into the receptor lymphs of this insect antenna by highly specific ((Pheromone Building Protein—PBP) or group specific (General Odorant Binding Protein—GOBP) proteins which themselves bind to the membrane resistant receptors or dendrites and, as a result, cause a depolarization of the neuron membrane. These depolarizations can be measured by high resistance semiconductor amplifiers such as field effect transistors. With a suitable signal and measurement value processing quantification of the responsible substance over a range in several orders of magnitude is possible.

The required selectivity and sensitivity of the biosensor system can be insured by a suitable selection of the biocomponents—type, breeding and preparation of the used antenna, for example an antenna from the family of the bark beetle. Because of the possibility to miniaturize the interface between the operative chemoreceptor and the semiconductor component the operational reliability of the biosensor system can be increased and, at the same time, volume-, weight- and energy requirements can be reduced. By a combination of such a biosensor system with commercially available gas sensors for typical combustion gases, the detection reliability can be substantially increased.

The invention will be described below in greater detail on the basis of the accompanying drawings.

BRIEF DESCRIPTION OF THE DRAWINGS

FIG. 1 shows schematically a biosensor system, and

FIG. 2 is an enlarged representation of the area of the biosensor system which is encircled in FIG. 1.

DESCRIPTION OF A PREFERRED EMBODIMENT

FIG. 1 shows the biosensor system including an operative chemoreceptor of a bark beetle. Such a system is usable for example in an early fire detection system.

The air to be measured is supplied through an admission pipe 1, which consists of a solid pipe or a pipe which is movable by way of ball joint and is comprised for example of glass, Teflon or stainless steel and has a diameter of up to 100 mm, preferably 5 to 15 mm leads to a sampling cell arrangement 2 of glass, Teflon or stainless steel. The sampling cell arrangement permits a simple and rapid change or exchange of the sensor module 5, 6 and provides for the mechanical stability which is necessary for a use of the sensor system as a mobile unit.

The sensor module 5, 6 and consequently, the biocomponent are located in a stable and protected position by means of suitable micro-mechanical locking, or respectively, mounting means 7. For even more increased protection from static disturbances the sensor module may be disposed in a miniaturized Faraday cage which is maintained at a stable electrical potential.

The sensor module 5, 6 is connected to a conductor plate substrate 8, which includes for example an opening 8a providing a flow passage for the air to be conducted past the biocomponent. For a mechanical stabilization of the antenna 5, an electrically insulated support structure 4 is provided on the opposite side of the opening 8a so that the antenna 5 bridges the opening 8a.

By way of a containment 9, which may act as a pulsation damper, the sensor air is sucked out of the sampling cell 2 by a pump 10 with a pumping volume adapted to the sampling cell arrangement which is for example 0–5 l/min, preferably 0.5–1.5 l/min. Instead of the pump arrangement (9,10) the natural movement of the air may be utilized; in case of a fire the draft generated by the fire or air diffusion may be relied on for supplying the fire emissions to the biosensor system.

The measurement signals obtained by the sensor module 5, 6 are transmitted to a signal processing unit 11 by way of conductors 11a which are preferably shielded. The resulting signal depends directly on the intensity of the detected fire "smell", that is, on the type and the concentration of the fire emissions or, respectively, on the plant emissions thereby indicating the extent and the type of the plant damage.

The biosensor 5b as shown in FIGS. 1 and 2 comprises a semiconductor component, preferably a field effect transistor (FET), for example a MOS-FET) of an insect antenna 5 for example an operational chemoreceptor 5 of a bark beetle or a potato beetle and a connecting unit which provides for the electric contact between the antenna and the FET.

The operative chemoreceptor 5 is contacted at one end by a conductor electrode 3 consisting for example of glass or a metal, preferably Ag, Pt or Ag/AgCl. At the other end, the chemoreceptor 5 is in direct electrical contact with the semiconductor component by means of a liquid or solid contact structure 14, preferably an electrolyte solution 14. In addition, an additional reference electrode of, for example, Ag/AgCl may be provided at this end in order to determine, together with the conductor electrode 3 at the one end, the immediate voltage drop at the insect antenna 5.

The antenna (operative chemoreceptor) 5 is supported in a mechanically and electrically stable manner by an antenna support arrangement consisting, for example, of a support plate 13 having an opening 13' through which the antenna extends, sealed by a viscous seal 12, into contact with the liquid or solid contact structure 14, that is, an electrolyte as shown in FIG. 2. It is advantageous if only as small a number of segments of the antenna as possible extends into the electrolyte so that a relatively long section of the antenna 5 is available for the detection of the trace components contained in the air conducted past the antenna 5. The support plate 13 is directly connected to the wall 15 in a mechanically stable manner and the wall 15 is directly connected to the semiconductor component and sealed by a seal 16, for example, an O-ring.

The semi-conductor component which is preferably an FET building element comprises a base substrate 21 of, for example, n- or, respectively, p-doped silicon. Depending on the doping of the base material, the pocket-like substrate areas 18 and 18a provided for the formation of source and drain have opposite doping. These substrate areas 18 and 18a are electrically connected to a solid support member such as the conductor plate substrate 8 by way of a contact structure 22 (for example of Ti/Al, Ti/Pd/AU or similar conductive material) which are disposed on the backside of the base substrate 21 and are electrically passivated and encapsulated. A metal layer 20 is provided on the substrate areas 18 and 18a which may be isolated from the base substrate 22 by an insulating layer or insulating layers 19 of $SiO_2$ or $SiO_2/Si_3N_4$ or $SiO_2/A_2O_3$ or similar layers.

Instead of the gate electrode usually provided with an FET, in the present arrangement the operative chemoreceptor is contacted by the electrolyte solution 14 which, at the same time, represents the biological nutrient solution for the antenna. Alternatively, instead of an electrolyte solution, other liquid or solid contact arrangements could be used. In the arrangement as shown in FIG. 1 and FIG. 2, a liquid resistive gate isolator 17, for example, of SiO$_2$ or SiO$_2$/Si$_3$N$_4$ or SiO$_2$/Al$_2$O$_3$ with a layer thickness of for example several nm is used. The direct contacting of the operative chemoreceptor by the semiconductor component substantially increases the reliability of the biosensor system because of the direct high-resistance low-noise signal amplification by the miniaturized FET used as the signal converter. This direct contact facilitates the provision of a fast and gentle biological connection that is one which does not detrimentally affect the hemolymphatic system of the antenna, and which, on one hand, transmits the signal reliably to the FET and on the other hand, keeps the effects of the autolysis reaction and the ion distribution inequities equities caused by the interference with the biologically operative erative system at a minimum. When the antenna provided as a sensor becomes inoperable, it can be replaced in a simple way by a new antenna suitably prepared for the application. In this way, the general arrangement can remain for repeated use.

With this relatively inexpensive and robust biosensor system on the basis of operative (live) chemoreceptors specific organic emissions generated, for example, by fires or by damaged plants can be detected with high selectivity and sensitivity. The combination of the biosensor system with a semiconductor sensor system combines the advantages of the two systems, that is, it has the high sensitivity and selectivity of the biosensor system as well as the long life and operational reliability of the semiconductor sensor system. In this way, early fire detection, for example, is facilitated. Also, measurement of plant damage on the basis of biological emissions can be performed on an agriculturally reasonably large scale as small space surveys by walking through an area or large area surveys such as infrared surveys from an airplane or satellite can be eliminated. It is possible to provide an arrangement in which the biosensor system is activated only after receiving an initiation signal from a semi-conductor sensor system arranged in parallel with the biosensor system.

What is claimed is:

1. A biosensor system for detecting trace compounds, said biosensor system comprising a sampling cell having means for conducting a sampling air flow carrying trace compounds through said sampling cell and including an operative (live) chemoreceptor for sensing said trace compounds, a semiconductor component connected to said chemoreceptor for providing sensor signals when said chemoreceptor senses the presence of trace compounds, said chemoreceptor being an insect antenna comprising a plurality of segments and being connected to said semiconductor component, said sampling cell including a plate with a flow passage for said sampling air flow, a container wall disposed on said plate adjacent said flow passage, a contact structure enclosed in said container wall, a support plate disposed on said container wall and having an opening receiving and supporting one end of said antenna such that only a small number of the antenna segments at said one end of said insect antenna is in contact with said contact structure enclosed by said container wall, said antenna having a portion extending from said support plate so as to be exposed to the air flow through said flow passage, and a conductor connected to said antenna portion extending from said support plate and leading to a signal processing unit.

2. A biosensor system according to claim 1, wherein only the last one of said antenna segments is connected to said semiconductor component.

3. A biosensor system according to claim 1, wherein said chemoreceptor is in communication with a signal processing unit by way of at least one electrode at at least one point.

4. A biosensor system according to claim 1, wherein said chemoreceptor is the antenna of a bark beetle.

5. A biosensor system according to claim 1, wherein said chemoreceptor is the antenna of a potato beetle.

6. A biosensor system according to claim 1, wherein said contact structure, by way of which said one end of said antenna is connected to said semiconductor component is an electrolyte.

7. A biosensor system according to claim 6, wherein said electrolyte is one of a solid and a liquid electrolyte.

8. A biosensor system according to claim 1, wherein said semiconductor component is a field effect based semiconductor insulator structure.

9. A biosensor system according to claim 8, wherein said chemoreceptor is connected to said semiconductor insulator structure in such a way that the connection forms a gate electrode of the field effect based semiconductor.

10. A biosensor system according to claim 8, wherein said chemoreceptor is connected to said semiconductor insulator structure in such a way that the connection forms a gate electrode of the field effect based semiconductor.

* * * * *